United States Patent
Han et al.

(10) Patent No.: US 7,670,833 B2
(45) Date of Patent: Mar. 2, 2010

(54) HIGH THROUGHPUT ANALYSIS FOR MOLECULAR FRACTIONS

(75) Inventors: Xiaoliang Han, San Francisco, CA (US); Jinming Xia, San Francisco, CA (US)

(73) Assignee: BioChain Institute, Inc., Hayward, CA (US)

( * ) Notice: Subject to any disclaimer, the term of this patent is extended or adjusted under 35 U.S.C. 154(b) by 832 days.

(21) Appl. No.: 10/636,853

(22) Filed: Aug. 6, 2003

(65) Prior Publication Data

US 2004/0029168 A1    Feb. 12, 2004

Related U.S. Application Data

(60) Provisional application No. 60/402,370, filed on Aug. 8, 2002.

(51) Int. Cl.
*C12Q 1/68* (2006.01)
*G01N 33/53* (2006.01)
*C12M 1/34* (2006.01)
*G01N 33/48* (2006.01)

(52) U.S. Cl. .................. 435/287.2; 435/6; 435/7.1; 435/287.3; 702/19; 702/20

(58) Field of Classification Search .................. None
See application file for complete search history.

(56) References Cited

U.S. PATENT DOCUMENTS

2003/0228371 A1* 12/2003 Skinner et al. .............. 424/530

OTHER PUBLICATIONS

MacBeath et al., Science, vol. 289, pp. 1760-1763, 2000.*
Reciprocal Net, Biochemical Molecules, printed from the Internet on Sep. 12, 2009 at <http://www.reciprocalnet.org/edumodules/commonmolecules/biochemical/list.html>.*

* cited by examiner

*Primary Examiner*—Shubo (Joe) Zhou
(74) *Attorney, Agent, or Firm*—Junrei Yang; Joe Zheng; Wuxi Sino-US IP Agency, Ltd.

(57) ABSTRACT

This invention presents the high throughput (HT) analysis technology for molecular fractions employing micro-array format. Molecules are fractionated according to the properties of molecules and are assigned primary designated orders while their tissue origins are assigned secondary designated orders such that each fractionated molecules become addressable and traceable. Fractionated molecules are recovered, arrayed, and analyzed according to the same primary designated orders and secondary designated order in a high throughput manner. The above properties of molecules can be measured and predicted.

30 Claims, 10 Drawing Sheets

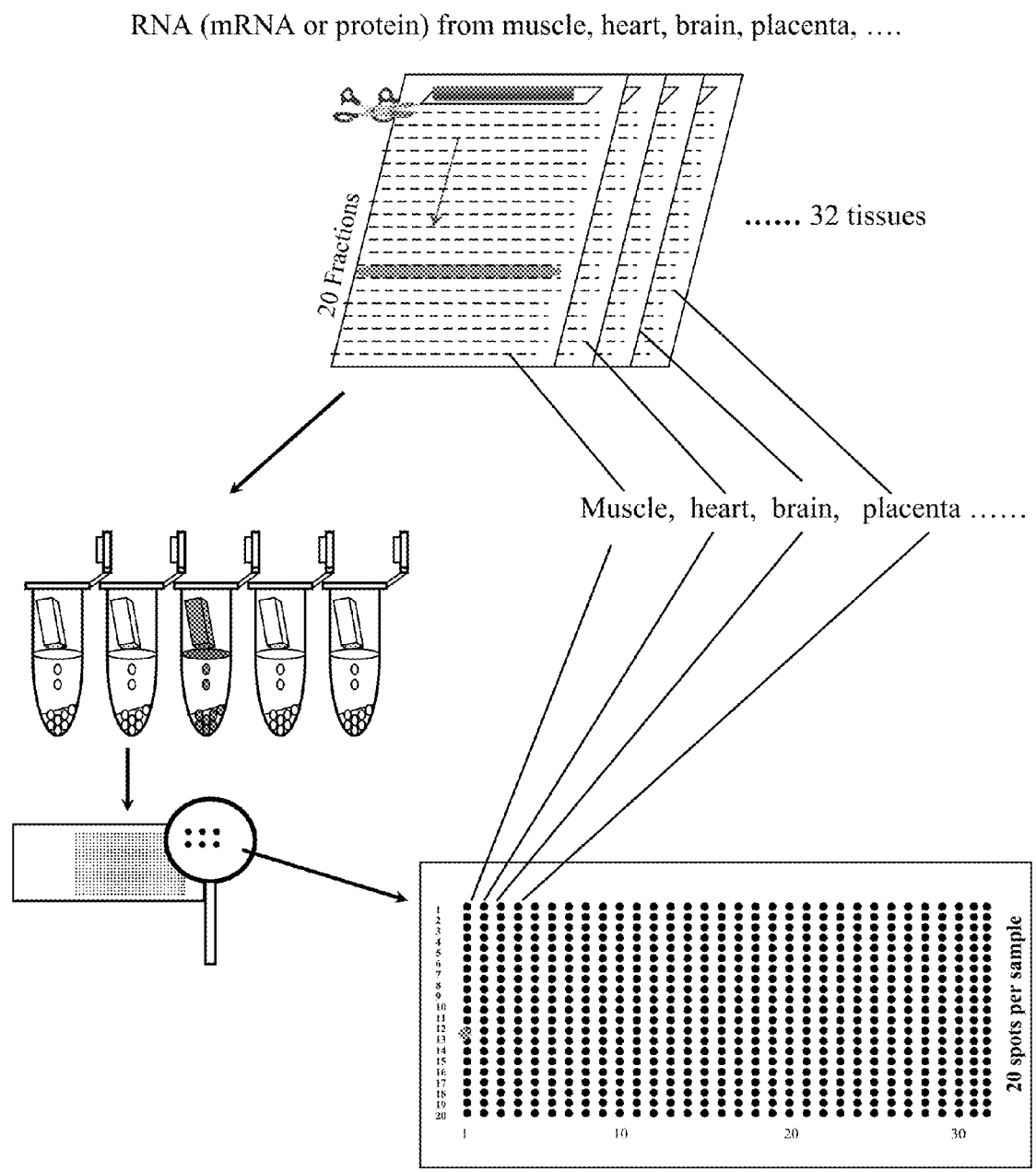
Fig. 1 Schematic Presentation of High Throughput Blot Techniques

Fig. 2 Fractioning mRNA by Gel Electrophoresis:
Together with RNA Ladder and Ruler as Size Indicator
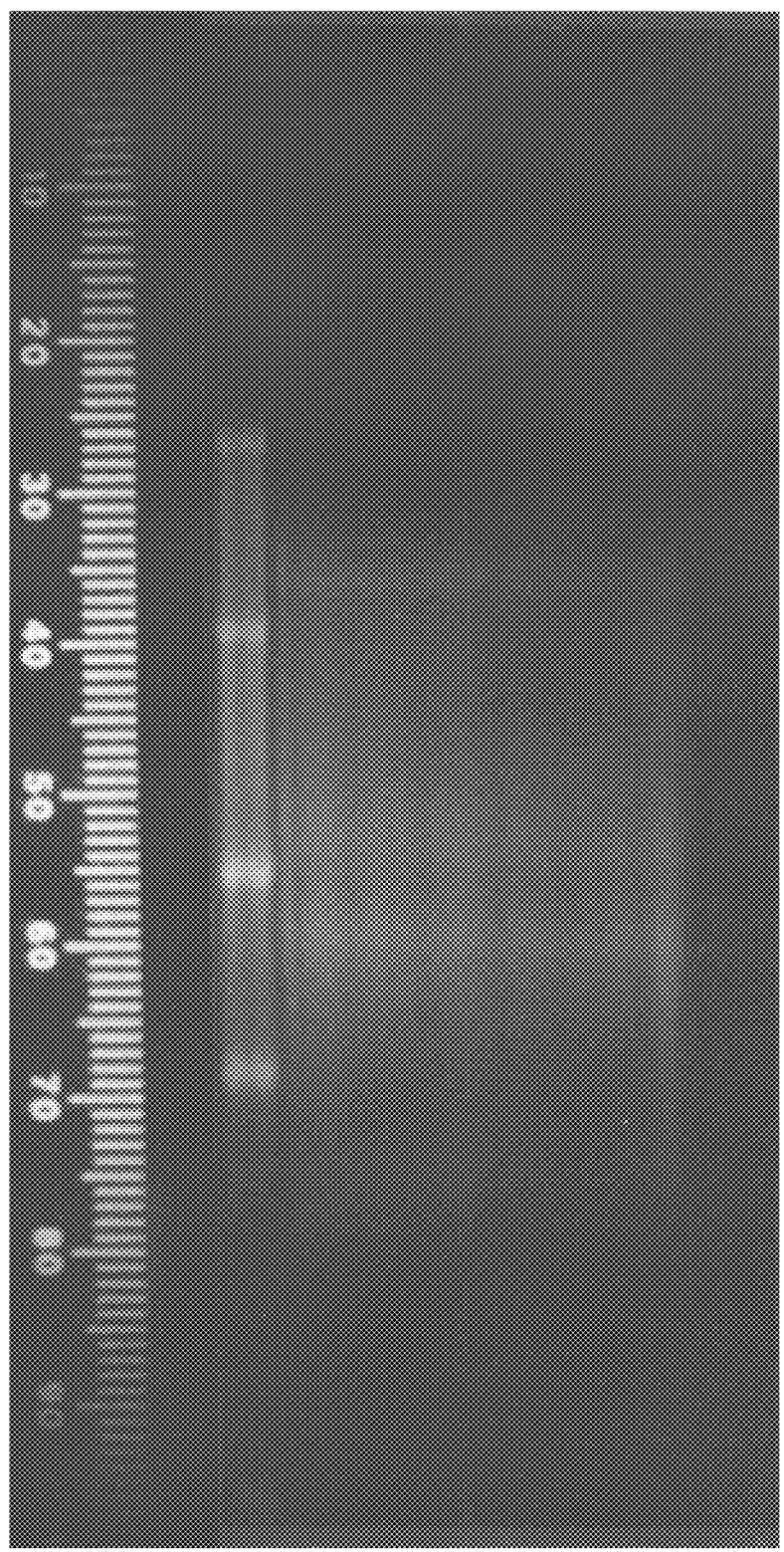

Fig. 3  Correlation Between the Migration Distance and Size of mRNA in 1% Agarose Gel Electrophoresis with Formaldehyde
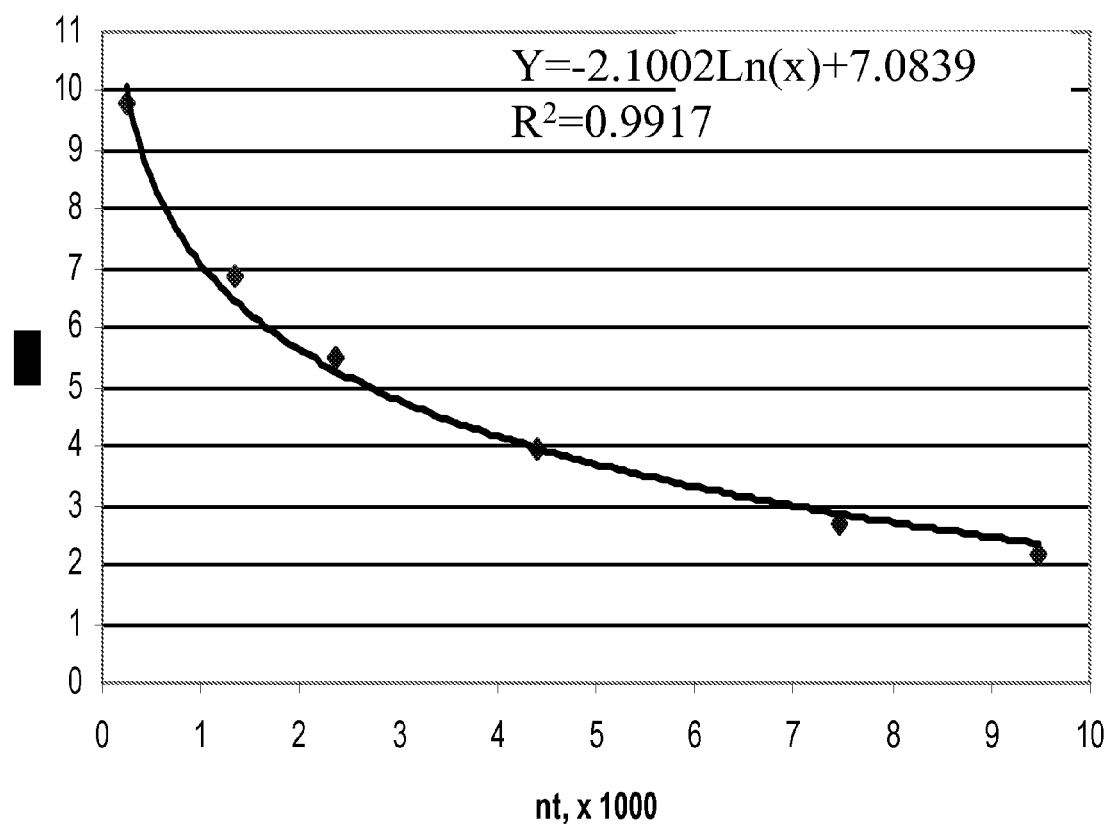

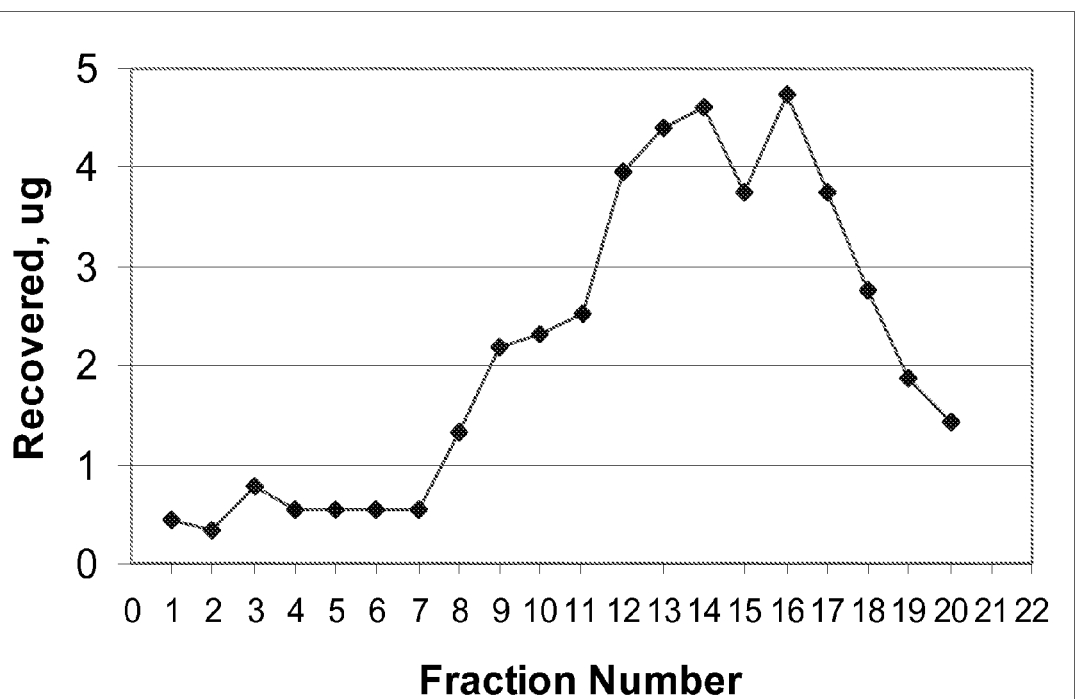
Fig. 4 Recovery Profile of Fractionated mRNA From The Serial Gel Fraction Slices Fig. 5 Fractionated mRNA from Human Placenta

Fig. 6  High throughput Northern Blot Analysis of 32 tissues
Panel A – Actual Size of Northern Blot
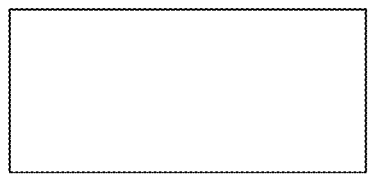
Actual Size: 1 x 2"
Panel B – Enlarged Panel A
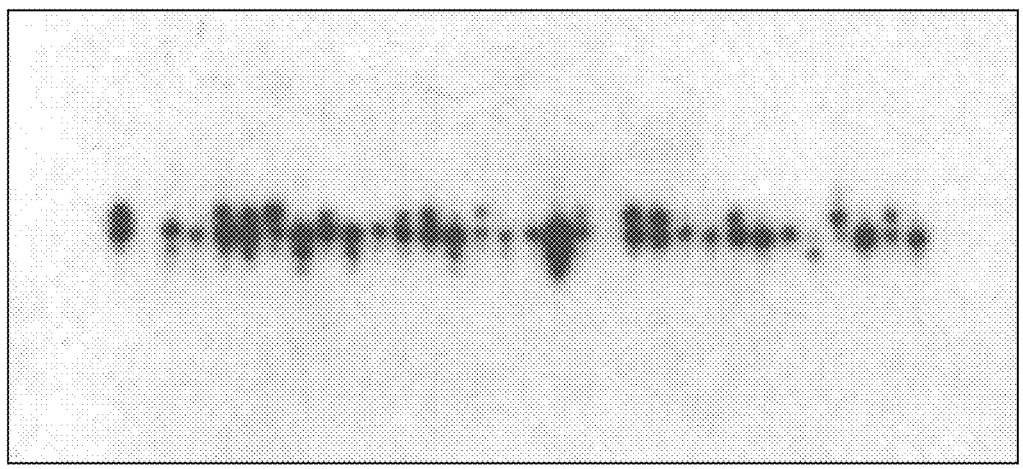

Fig 7. Comparison of Gene Expression Pattern between High Throughput Northern Blot and Conventional Northern Blot
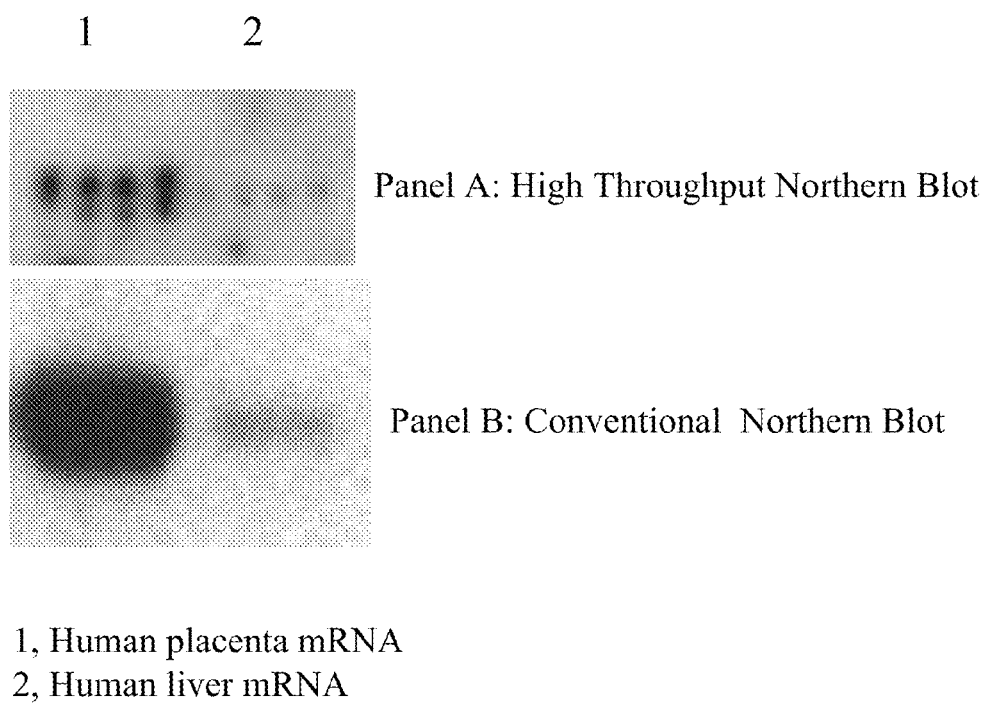
Panel A: High Throughput Northern Blot
Panel B: Conventional Northern Blot
1, Human placenta mRNA
2, Human liver mRNA Fig. 8 Comparison of sensitivity between
High Throughput Northern Blot and
Conventional Northern Blot
0.3   3 µg
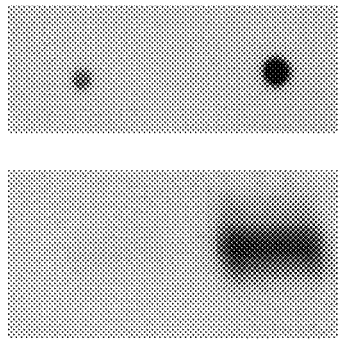
Panel A:  High Throughput Northern Blot
Panel B:  Conventional Northern Blot Fig. 9 Fractionated Protein From Human Liver Tissue
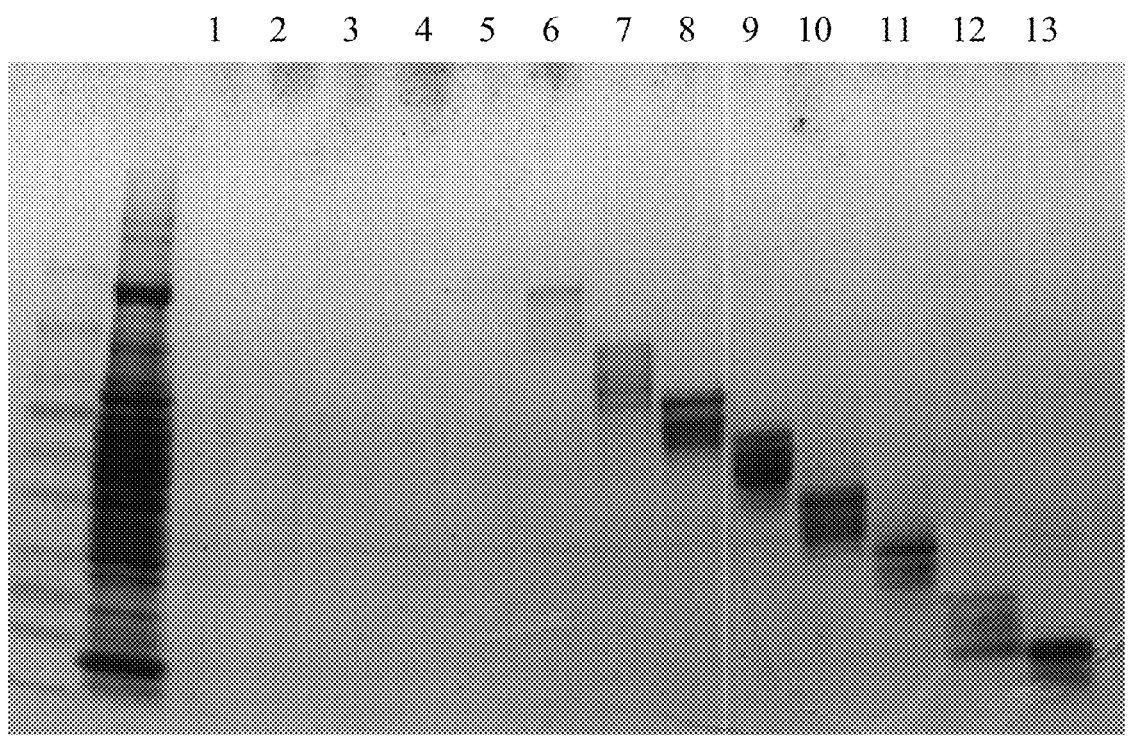

Fig. 10 High Throughput Western Blot Analysis of 16 Tissues in Duplicates
Panel A – Actual Size of Northern Blot
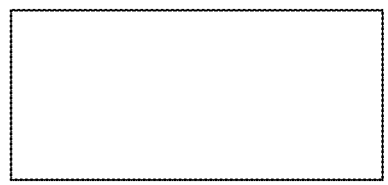
Actual Size: 1 x 2"
Panel B – Enlarged Panel A
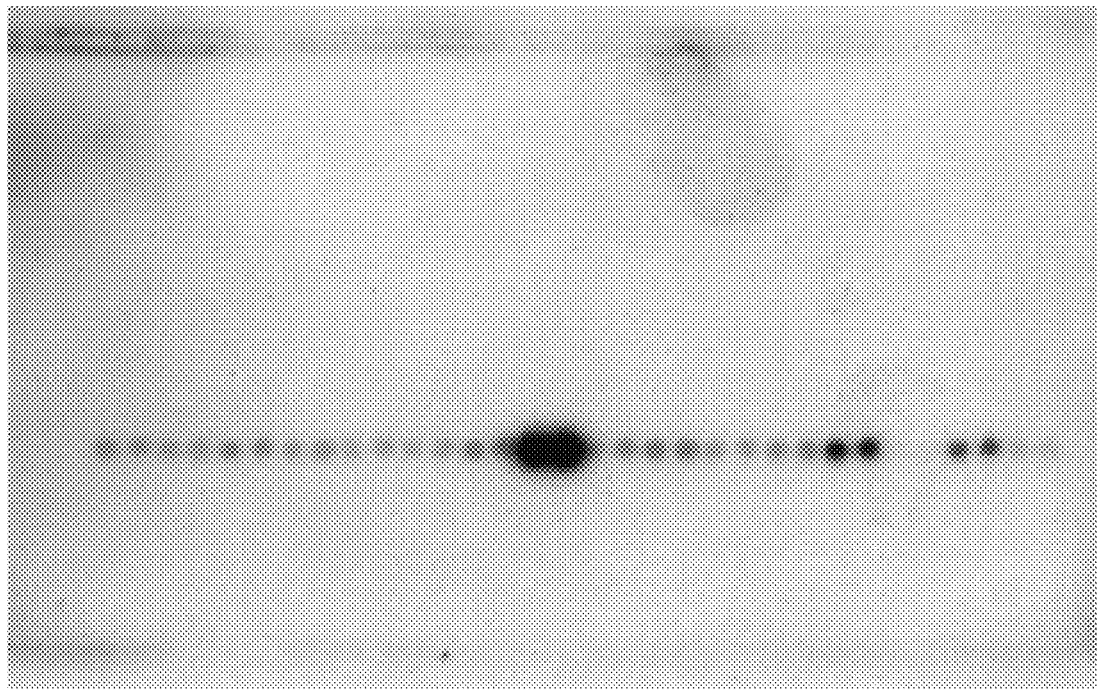

HIGH THROUGHPUT ANALYSIS FOR MOLECULAR FRACTIONS

CROSS-REFERENCE TO RELATED APPLICATION

This application claims the benefit of the filing date of U.S. provisional application Ser. No. 60/402,370, filed Aug. 8, 2002.

FIELD OF THE INVENTION

This invention relates to a method for high throughput analysis of molecular fractions. More specifically, it relates to a method for high throughput (HT) detection of presentation of molecular fractions.

BACKGROUND OF THE INVENTION

Analyses of molecular fractions of biologically significant molecules in desirable forms from biological origins have always been an important task for biochemical research. Molecules, such as ribonucleic acid (RNA), deoxyribonucleic acid (DNA) or cDNA, protein, peptide, lipids or polysaccharides, are usually required to be fractionated based on their biochemical properties such as size and charge before further accurate or meaningful analyses. Fractionating methods are those that can fractionate molecules and generate a spectrum or a serial fractions of molecules based on one or more properties of molecules, which methods include agarose gel electrophoresis, polyacrylamide gel electrophoresis (PAGE), two-dimensions PAGE, isoelectrical focusing, ion exchange chromatography, filtration chromatography, hydrophobic chromatography, high performance liquid chromatography (HPLC), thin layer chromatography (TLC), gas chromatography, atomic absorption, affinity chromatography or gradient centrifugation. With above fractioning methods, molecules can be fractionated according to their properties, such as molecular size, charges, organic phase solubility, affinity, mass, shape, density or color.

For examples, the conventional Northern blot analysis and Western analysis are the most widely used and vital techniques for analyzing sizes and amounts of RNA or protein molecules from biological origins. Northern blot (for RNA analysis) and Western blot (for protein analysis) are named after Southern blot (for DNA analysis), (Southern, E. M. 1975. Detection of specific sequences among DNA fragments separated by gel electrophoresis. J. Mol. Biol. 98:503-517, which is incorporated herein by reference). They have been the must or ultimate assays of choice to detect the sizes and expression level of certain genes in some cell populations or tissues. Although there are some other methods, such as differential display, RT-PCR or RNA protection assay (RPA) that can be used for part of this purpose, Northern blot analysis and Western blot analysis are the distinguished assays that can determine the molecular size or weight of the target gene or protein. The other methods are generally less favorable and more disadvantageous as they tend to produce unreliable results introduced as a result of complicated or enzymatic manipulation. Since Northern blot analysis and Western blot analysis are the closest methods to confirm real-life situation of gene or protein expression because they are rather direct measurement than other methods, they are ultimately important tools in determining sizes of alternative spliced gene, post translational modification of proteins as well as levels of gene or protein expression.

It has been many years for people to make and use conventional Northern blot and Western blot. Up to today, the ways to make conventional Northern blot analysis and Western blot are still the same as many years ago. When making Northern blot, RNA electrophoresis is performed using agarose gel with denaturing agents such as formaldehyde and formamide. Since RNA molecules carry one negative charge per molecule, their migration in agarose gel depends on the length of nucleic acids or the size of the molecules. Fractionated nucleic acids on the gel can be blotted to nylon or nitrocellulose membranes to make Northern blot. Probes that contain labeled nucleotides and are complementary to the target nucleic acid chain can be added for hybridization and detection of specific RNA fraction in Northern blot. It is Northern blot analysis to make it possible for estimating the size and the relative amount of a fraction of RNA simultaneously.

It is different to make Western blot from Northern blot because properties of protein are different from RNA. Proteins may carry negative or positive charges, depending on their amino acid compositions. In order to generate a uniform spectrum or serial fractions of proteins based on the molecular weight, sodium dodecyl sulphate (SDS), dithiothreitol (DTT) and β-mecarptoethanol are added to protein loading buffer and the gel. SDS is an anionic detergent that binds to proteins fairly specifically in a mass ratio of 1.4:1 and confers a negative charge to the protein in proportion to its length. All protein molecules become negative charged uniformly in present of SDS. In addition, reducing reagents such as dithiothreitol (DTT) and β-mecarptoethanol can disrupt the disulfide bonds of protein molecules to overcome the affect on gel electrophoresis by non-uniformed structures of protein. After gel electrophoresis, the gel can be stained or the protein can be transferred to a membrane to make Western blot. To detect particular fractions of proteins on Western blot, antibodies specific for the target proteins (antigens) are incubated with the membrane. The bound antigen-antibody complex is further detected by chemiluminescent, fluorescence or radioactive method. As Northern blot analysis, Western blot analysis is also capable of determining the size and relative amount of target proteins simultaneously.

While the conventional Northern blot analysis and Western blot analysis are the major tools for the afore-mentioned purposes, they are nevertheless limited as to the number of samples that can be applied on one membrane. It is generally agreed that fewer than ten samples can be accommodated on one membrane, which limitation renders the use of Northern or Western blot analysis for a large-scale, high throughput analysis of molecular fractions unfeasible.

The demands for high throughput analysis of molecular fractions become urgent with the discovery of more than 30,000 new genes due to the completion of the human genome project. U.S. Pat. Nos. 6,582,969 and 6,576,478 (Wagner et al) disclose a method and microdevices for high throughput screening of biomolecules. These microdevices comprise a certain arrayed of specially micromachined or microfabricated channels with a plurality of built-in noncontiguous reactive sites that are provided with biological moieties immobilized on a monolayer via an affinity tag linked to a substrate. These microdevices are capable of screening functionality or structurally related components passing through the channels. U.S. Pat. No. 6,537,749 (Kuimelis et al) discloses addressable protein arrays in which arrays of nucleic acid-protein fusions are immobilized to a solid surface through a linker layer that is provided with a spacer group on one end and an oligonucleotide sequences on the other end for interacting with an addressable array of molecules complementary to the immobilized oligonucleotide sequences.

While these arrayed techniques may be sufficient to provide high throughput screening of biomolecules, they have to be specially constructed with desirable immobilizing agents and affinity groups. In addition, none of these techniques aims at the incorporation of the advantages of conventional Northern blot analysis and Western blot analysis as described above, such as size of mRNA or protein molecules, while improving their shortcomings to develop a high throughput screening system capable of screening a substantial amount of samples with more detection sensitive and consuming less treasured materials.

For the foregoing reasons, there is an apparent need for a method and device for high throughput screening of molecular fractions that combines the unique features of molecular fractionating technique and the power of micro-array.

There is a further need for a method and device for high throughput screening of molecular fractions that creates a more sensitive method in detection of certain desirable biological activity while consuming less treasured materials Accordingly, this present invention provides a solution to create a high throughput screening system, such as incorporating both Northern blot analysis and Western blot analysis as illustrated above, while provided with molecular fractionating methods and properties based to fractionate molecules fundamentally different.

SUMMARY OF THE INVENTION

The present invention relates to a high throughput analysis technology for molecular fractions that uses array format. This high throughput technology brings conventional techniques for the analysis of molecular fractions, such as Northern blot, Western blot, Southern blot, and protein 2-D blot, to a high-throughput platform using an array format. Molecules, whether they are DNA, RNA, protein, peptide, lipids or polysaccharides, are fractionated based on their biochemical properties such as size and charge. Fractionated molecules from plentiful samples are each assigned simultaneously with a primary designated order and a secondary designated order and are recovered according to such primary designated order and secondary designated order, and rearranged onto supporting materials in the same primary designated orders and secondary designated order.

To illustrate present invention, molecular weight or size is served herein as example of the properties of mRNA and protein, to which the molecules are fractionated accordingly. Then, using various detection methods suitable for the targeted molecules, the properties (molecular weight or size) of uncharacterized mRNA and protein can be measured and predicted. Because molecular weight or size is the crucial component of the gene expression patterns, with the present invention, presentation patterns of each fractionated molecule among plenty of tissues, such as gene expression, can be analyzed by following the same primary designated orders and secondary designated order described above in a high throughput manner.

Replacing of conventional Northern blot or Western blot analyses is not the only application of this invention. This invention can apply to many analyses of molecular fractions fractionated by a variety of fractionating methods according to different properties of molecules. Molecules involved in this invention are, but not limited to, nuclear acid, such as ribonucleic acid (RNA), deoxyribonucleic acid (DNA) or cDNA, protein, peptide, lipids or polysaccharides. Fractionating methods covered by this invention are those that can fractionate molecules and generate a spectrum or a serial fractions of molecules based on one or more properties of molecules, which include agarose gel electrophoresis, polyacrylamide gel electrophoresis (PAGE), two-dimensions PAGE, isoelectrical focusing, ion exchange chromatography, filtration chromatography, hydrophobic chromatography, high performance liquid chromatography (HPLC), thin layer chromatography (TLC), gas chromatography, atomic absorption, affinity chromatography or gradient centrifugation. With above fractioning methods, molecules can be fractionated according to such properties of molecules, as molecular size, charges, organic phase solubility, affinity, mass, shape, density or color. As long as molecules can be fractionated to generate a spectrum or a serial fractions of molecules, this invention can apply.

One embodiment of the present invention is to provide for a method of analyzing a plurality of molecular fractions from a population of molecules from or within the same or different origin(s) in high throughput manner. The method comprises the step of fractionating each of said plurality of molecular fractions into a spectrum or a group of serial fractions containing sub-populations of serial fractionated molecules according to properties of said fractionated molecules by one or more fractionating methods. Prior to or simultaneously with the step of fractionating, each of the spectrums or the group of serial fractions is assigned a primary designated order and a secondary designated order. The primary designated order is assigned according to parameters, such as distance, timing; or order, of said fraction being arranged or present in a fractionating media used by the fractionating methods. More specifically, the distance or timing that used to assign the primary designated orders can be either the migration distances of the fractionated molecules on the fractionating media or the distance where the fractionated molecules run-out from said fractionating media or the time required thereof. The primary designated orders can be recorded as any natural order formed by said group of serial fractions based on the distance and timing of the fraction arranged in the fractionating media or can be based on a rearranged order.

According to the present invention, the fractionated molecules may be mixtures of similar or different molecules with similar or different properties based on which a spectrum or a group of serial factions can be obtained after a proper fractionating process. In particular, the fractionated molecules include, but not limited to, nuclear acid (DNA, cDNA or RNA), protein, peptide, lipid or polysaccharides, which may be fractionated and subsequently recovered at their original forms or at forms amenable for further manipulation. The properties of the fractionated molecules, that are frequently used to obtain desirable fractionation, include, but not limited to, molecular size, charges, solubility, weight, density, affinity, mass or color. The fractionating methods suitable for the present invention include a variety of separating methods selected from the group consisting of agarose gel electrophoresis, polyacrylamide gel electrophoresis (PAGE), two-dimensions PAGE, isoelectrical focusing, ion exchange chromatography, filtration chromatography, hydrophobic chromatography, high performance liquid chromatography (HPLC), thin layer chromatography (TLC), gas chromatography, atomic absorption, affinity chromatography or gradient centrifugation. It should be noted that any one method from the group or a combination of two or more separating methods from this group can be properly used to fractionate the molecular fractions according to the present invention. In addition, when there is a need to select a cut-off point for the molecular fractionation, an arbitrary set of cut-off points such as the molecular sizes of the molecules referred by the accompanying molecular weight standards can be used. In this regard, the arbitrary set of cut-off points can be established based on a linear, logarithm, or exponential relationship of said accompanying molecular weight standards.

One more aspect of the invention is to provide for a method of recovering the serial fractionated molecules from the group of serial fractions off the fractionating media upon the completion of fractionating. In order to clearly identify and relate the recovered molecules to the plurality of molecular fractions from which they are originally recovered, as well as to provide convenience for the serial fractionated molecules to be subsequently manipulated in a high throughput manner, each of the serial fractionated molecules is assigned and accorded with exactly the same primary designated order and the secondary designated order as the one assigned to each of the group of serial fractions from which this particular fractionated molecule is recovered. Accordingly, the serial fractionated molecules have the same "designated addresses" as the corresponding group of serial fractions in relation to their initial lineups or present in the fractionating media. Thus, the present invention provides a unique feature by establishing an "addressable" mechanism to track and relate the serial fractionated molecules recovered thereto to the corresponding group of serial fractions, which mechanism is further extended to subsequent placement and arraying of the recovered molecules onto a supporting material suitable for high throughput manipulation. It should be noted that the recovering step described above could be optionally performed without the need of separating the serial fractionated molecules from said fractionating media. In addition, the recovering step can be automated or be done at the aids of kits or devices commercially available.

Another aspect of the invention is to provide for a step of arraying the serial fractionated molecules onto a supporting material according to their corresponding primary and secondary designated orders such that the serial fractionated molecules are always capable of being addressed back to their corresponding group of serial fractions. Arraying the serial fractionated molecules to the supporting material can be automated by using micro-arrayers or by manually with or without any devices. The total number of fractions containing the fractionated molecules arrayable with the primary and secondary designated orders to the supporting material can be ranged from two to over 500,000 fractions per piece of the supporting material according to the present invention. Additionally, this arraying step may be optionally performed in an arbitrary order. The supporting material could be selected from a variety of materials known to the art. However, in one preferred embodiment, the supporting material is selected from the group consisting of nitrocellulose, nylon, plastic, glass, multi-well plates and beads. Furthermore, the supporting material can be further treated to have a charge thereof or be chemically modified to carry a molecules binding enhancer such as ploy-lysine or to cause the supporting material be silylated and silanated according to the invention.

One more aspect of the invention is to provide for a step of designing and selecting probing molecules that can interact and bind to the serial fractionated molecules arrayed on the supporting material. This step may further comprise a step of performing incubations or hybridizations of the probing molecules with the arrayed fractionated molecules on the supporting material. Upon the completion of the incubations or hybridizations, the amount of probing molecules on the supporting material is determined by a detection method, such as either one of chemical, chemiluminescent, fluorescent or radioactive method. According to the present invention, the probing materials can be RNAs, DNAs, proteins, antibodies or chemically modified proteins with a chemical or fluorescent label or radioactive isotope. The detection of the amount of probing molecules can be performed manually, such as exposing a regular film in laboratory if the spots of fractionated molecules are few in number or by instruments such as micro-array scanners if there are substantial and many spots of fractionated molecules on the supporting material.

One additional aspect of the invention is to provide for a step of analyzing and correlating presentation patterns of the arrayed fractionated molecules in according to their corresponding primary and secondary designated orders. Analyzing of the presentation patterns of the serial fractionated molecules is preferably performed by mathematical calculation along with a computerized image and data analysis in a high throughput fashion to generate desirable database. The mathematical calculation can accurately determine the migration distance or run-out time of the serial fractionated molecules in or from the fractionating media according to the primary and secondary designated orders and the computerized image and data analysis can accurately determine the amount of each of the serial fractionated molecule according to the primary and secondary designated orders. Furthermore, the computerized image and data analysis can enlarge the image of micro-array spots of the serial fractionated molecules. Consequently, the amount of fractionated molecules needed for the step of computerized image and data analysis according to the invention is far more less than that needed for conventional Northern blot analysis or Western blot analysis. Likewise, the step of arraying the serial fractionated molecules directly onto the supported material according to the invention generates stronger signals that significantly increase detection sensitivity as compared to the detection sensitivity of the conventional methods such as the Northern blot analysis or Western blot analysis. Since the step of computerized image and data analysis can directly collect, analyze and convert information from the fractionated molecules into dependable database and since this invention further permits the application of plentiful groups of serial fractionated molecules from a plenty of samples, such as many tissue samples to create high throughput analysis platform for fractionated molecules, which can not be achieved by the conventional Northern blot analysis or Western blot analysis.

One additional embodiment of the present invention is to provide for a method of generating molecular fractions from a population of molecules from or within the same or different origin(s) suitable for further manipulation in a high throughput manner. This method comprises the steps of (1) providing a plurality of molecular fractions from the same or different origins in a form ready to be fractionated; (2) fractionating each of the plurality of molecular fractions into a spectrum or a group of serial fractions containing sub-populations of serial fractionated molecules by at least one fractionating methods wherein each of said spectrum or said group of serial fractions is assigned a primary designated orders and a secondary designated order and the primary designated orders is assigned according to parameters, such as distance, timing, or order of said fraction being arranged or present in a fractionating media of said fractionating methods; (3) recovering the serial fractionated molecules from the group of serial fractions off the fractionating media such that each of the serial fractionated molecules is accorded with the same primary and secondary designated orders as each of the group of serial fractions from which it is recovered; and (4) arraying the serial fractionated molecules onto a supporting material according to their corresponding primary and secondary designated orders in step (2) to be manipulated for further purposes.

Still one additional embodiment of the present invention is to provide for a method of profiling representation patterns of molecular fractions prepared from a variety of different origins in a high throughput manner. More particularly, this method permits the comparison of representation patterns of molecular fractions prepared from a variety of different origins such as from different cells or tissues. Since all the molecular fractions are treated under the same conditions, this method provides a useful tool to profile a particular representation pattern or a particular biological activity across a variety of tissues in a high throughput manner. In practice, this method comprises the steps of providing a plurality of molecular fractions from said variety of different origins in forms ready to be fractionated; fractionating each of said plurality of molecular fractions from one origin, such as from one piece of tissue specimen, into a spectrum or a group of serial fractions containing sub-populations of serial fractionated molecules according to their properties by at least one fractionating methods wherein each of said spectrum or said group of serial fractions is assigned a primary and a secondary designated orders wherein the primary designated orders is assigned according to parameters, such as distance, timing, or order of said fraction being arranged or present in a fractionating media of said fractionating methods and wherein the secondary designated order is assigned according to origin of the specimen (such as the specimen from brain, liver, etc); repeating fractionating each of said plurality of molecular fractions from all said variety of different origins; recovering the serial fractionated molecules from said group of serial fractions from one origin off the fractionating media such that each of said serial fractionated molecules is accorded with the same primary and secondary designated orders as each of said group of serial fractions from which it is recovered; repeating recovering the serial fractionated molecules from said group of serial fractions from all said variety of different origins; arraying the serial fractionated molecules from all said variety of different origins onto a supporting material according to their corresponding primary designated orders and secondary designated orders to be manipulated further; designing and selecting desirable probing molecules intended to interact with the serial fractionated molecules arrayed on the supporting material to obtain desirable representation patterns of the arrayed fractionated molecules from said variety of different origins; and analyzing and comparing said presentation patterns characteristics of the arrayed fractionated molecules from said variety of different origins according to their corresponding primary designated orders and secondary designated order.

Accordingly, this invention combined the unique feature of molecular fractionating technique and the power of micro-array or macro-array. Beyond the feature of conventional molecular fractionating technique, this invention creates a more sensitive method while consuming less treasured materials. The most important benefit provided for by the present invention is that up to hundred or thousands of samples can be analyzed in a high throughput way for molecular fractions, such as alternative splicing or sizing of a specific gene among hundreds of different tissues, on a micro-array or macro-array. Furthermore, the information about molecular fractions can be digitized and collected directly by array scanner and convert into database, and data analysis can be accommodated into micro-array detection technology platform.

This present invention can be applied at least to both Northern blot analysis and Western blot analysis as illustrated in previous paragraph, although the molecules, fractionating methods and properties based to fractionate molecules are fundamentally different. Something in common between these two methods is that molecules can be fractionated to form a spectrum or serial fractions. The core concept of this invention is to convert the spectrum or serial fractions into array format. Therefore, this invention can be applied to a variety of molecules as long as it can form a spectrum or serial fractions by different fractionating methods.

BRIEF DESCRIPTION OF DRAWINGS AND FIGURES

The present invention will be better understood and the nature of the objectives set forth above will become apparent when consideration is given to the following detailed description of the preferred embodiments. For clarity of explanation, the detailed description further makes reference to the attached drawings herein:

FIG. 1 shows the main steps involved in HTS Northern/Western blot analysis where protein or mRNA isolated from different tissues is fractionated by gel electrophoresis wherein the gel containing different fractions is cut into many (in this case, 20) fractions and the fractionated molecules in the gel fractions are recovered by means of gel extraction or elution; one group of serial fractionated molecules from one type of tissue, such as muscle, are arrayed on membrane supported by microscopic slide in the same order as presented inside the gel before and many groups of serial fractionated molecules from many different tissues, such as muscle, heart, brain, placenta, etc, can be arrayed on the same membrane;

FIG. 2 shows the separation or fractionating of mRNA on agarose gel wherein 100 µg of human placenta mRNA are separated in 1% formaldehyde agarose gel; the distributions of mRNA species are most abundant in the middle range of the gel and RNA ladder and ruler serve as marker to calculate the size of RNA fractions;

FIG. 3 shows the relationship of migration distance and molecular size of mRNA wherein migration distance of mRNA (in cm) and molecular size of mRNA (in number of nucleotides) have a logarithm relationship after curve fitting the two parameters with a $R^2=0.9917$;

FIG. 4 shows the amount of mRNA recovered from each of 20 fractions as measured by UV spectrophotometer wherein fractions 8 to 20 contain relatively more mRNA than that of fractions 1 to 7, which is consistent with the relative abundance of mRNA in different locations of gel showed by FIG. 2;

FIG. 5 is gel picture of fractionated RNA that shows the relative amounts and the size of fractionated mRNA in every fraction from human placenta mRNA wherein fractions 8 to 20 contain more mRNA than the rest of the fractions and is consistent with the relative abundance of mRNA in different locations of gel showed by FIG. 2;

FIG. 6 shows the relative gene expression of mRNA samples prepared from 31 different tissues by high throughput Northern blot analysis on a membrane in the size of microscopic slide where variations of hybridization signals indicate the different expression patterns of GAPDH in these tissues wherein Panel A is the actual size of high throughput Northern blot and Panel B is 9× enlargement to visualize by naked eye; and tissues on blot from left to right are 1. Placenta; 2. negative control; 3. Bladder; 4. Brain; 5. Brain, Frontal lobe; 6. Brain, Hippocampus; 7. Brain, Occipital lobe; 8. Brain, Parietal lobe; 9. Brain, Temporal lobe; 10. Breast; 11. Cerebellum; 12. Colon; 13. Esophagus; 14. Heart; 15. Kidney; 16. Liver; 17. Lung; 18. Muscle; 19. Ovary; 20.

Pancreas; 21. Placenta; 22. Rectum; 23. Skin; 24. Small Intestine, duodenum; 25. Small Intestine, Ileum; 26. Small Intestine, Jejunum; 27. Spleen; 28. Stomach; 29. Testis; 30. Tonsil; 31. Uterus, Cervix; and 32. Uterus, Corpus;

FIG. 7 shows the different expression patterns of GAPDH in human placenta mRNA and human liver mRNA by high throughput Northern analysis (panel A) and by conventional Northern analysis (Panel B) wherein both high throughput Northern analysis and conventional Northern analysis present similar gene expression patterns in which relative amount of GAPDH mRNA is much more abundant in human placenta than that in the liver and quadruplets of spots in high throughput Northern analysis show the consistency and the precision of the method;

FIG. 8 shows that high throughput Northern blot analysis has higher sensitivity in detecting mRNA expression than conventional Northern method where 0.3 µg of starting mRNA is subjected to gel electrophoresis and transferred to nylon membranes wherein the conventional Northern blot analysis method failed to detect the expression of GAPDH as shown in Panel B while high throughput Northern blot analysis of the equivalent amount of the same sample showed the stronger signals in Panel A.

FIG. 9 shows the elution profile of whole proteins, stained by Coomassie brilliant blue, from human liver tissue after being fractionated on a preparatory 4-20% gradient gel wherein multiple fractions are eluted simultaneously in a uniform electric field and each fraction includes fractionated protein from a fixed length of gel (0.5 cm); and FIG. 10 shows the relative protein expression of GAPDH in 16 different human tissues by high throughput Western blot where the fractionated proteins are recovered from whole proteins of 16 different human tissues and reapplied at the primary designated orders and secondary order on membrane and GAPDH signal from high throughput Western blot analysis is detected at correct molecular size in the expected fraction wherein Panel A is actual size of high throughput Western blot; Panel B is 9× enlargement to visualize by naked eye and tissues on blot from left to right are 1,2 heart, 3,4 brain, 5,6 kidney, 7,8 liver, 9,10 lung, 11,12 pancreas, 13,14 spleen, 15,16 skeletal muscle, 17,18 stomach, 19,20 small intestine, 21, 22 colon, 23, 24 rectum, 25, 26 uterus, 27, 28 prostate, 29, 30 testis, and 31, 32 placenta.

DETAILED DESCRIPTION OF THE INVENTION

The present invention provides a method for high throughput (HT) analysis of presentation patterns of molecular fractions, such as gene expression in biological samples, in an array format. In a preferred embodiment of the invention, gene expression at messenger RNA (mRNA) level or at protein level is used to illustrate present invention.

The following materials are employed to illustrate present invention: 1) Microarray devices: A 32 pin Glass Slide Microarrayer (VP478A) and its accessories, a indexing unit (VP470) and a microplate indexer (VP472A), were purchased from V&P Scientific (San Diego, Calif.); 2) Whole gel eluter (165-1251): Bio-Rad Laboratories (Hercules, Calif.); 3) RNAID: from Qbiogene (Carlsbad, Calif.) is used to extract mRNA from the gel; 4) Membrane: Hybond N+ (Positively-charged nylon Membrane) from Amersham Biotech; 5) PCR kit: Promega Corp. (Madison, Wis.). DNA polymerase and PCR buffer; 6) Hybridization buffer: The buffer compositions are based on Church and Gilbert (Church, 1984) and contains the following: 1% BSA, 0.5M sodium phosphate buffer, pH 8.0, and 7% sodium dodecyl sulfate (SDS); 7) Detection kit: CDP-star AP substrate and anti-fluorescein AP conjugate antibody (Cat. No. 1064285) from Amersham Biotech; 8) 0.24-9.5 Kb RNA ladder (Cat. No. 15620-016) from Life Technologies; and 9) Fluorescein-12-dUTP (Cat. No. 1373242) from Roche Molecular Biochemicals.

To develop a HT method for the detection of gene expression at the messenger RNA (mRNA) level or at protein level, HT Northern blot or HT Western blot in array format are invented as one embodiment of this invention. The term "HT Northern blot" or "HT Western blot" means the detection and analysis of mRNA or protein from blots containing mRNA or protein prepared from a lot of different specimens in fractionated and arrayed populations in principle and application like conventional Northern blot or Western blot made from only very few specimens. But the way of transferring fractionated molecules, such as mRNA or protein in present invention, is fundamentally different from the existing techniques to make conventional Northern blot or Western blot.

The concept of invention is illustrated in FIG. 1 in a flowchart format, which shows the main steps involved in HT Northern/Western blot analysis. Protein or mRNA isolated from different tissues is fractionated by gel electrophoresis. The gel containing different fractions of protein or mRNA is cut into many fractions as desirable. In the embodiment illustrated in FIG. 1, the gel containing different fractions of protein or mRNA isolated from muscle is cut into 20 fractions. Each fraction is designated by a number based on its corresponding distance and order (parameters) initially presented in the gel. Accordingly, each fraction becomes addressable after being designated with such number (primary designated order), such that each fraction is recorded with its primary designated order and, as a result, the entire fractions derived from the gel are properly ordered and addressable according to their initial migrating distances and sequential or serial orders presented in the gel. Simultaneously with the designation of the primary designated order to each of the fractions, a second number (which may be a numerical number, a symbol, an abbreviation or a character) is also assigned to each of such fractions from the same gel as a secondary designated order to specifically identify the origins of the specimens or the type of tissues or cells from which such fractions (or the fractionated molecules) are derived. In particular, the secondary designated orders are indispensably useful when a substantial number of specimens of different origins, such as the specimens from muscle, liver, heart, brain etc., are subject to the high throughput analyses according to the present invention as will be fully described hereunder.

By way of illustration and not intended to be limited, the fractionating processes as described above are repeated on different specimens to generate different groups of fractionated molecules for further applications. For examples, as shown in FIG. 1, these processes are repeated 31 times on mRNA from 31 different human tissues such as Placenta; Bladder; Brain; Brain, Frontal lobe; Brain, Hippocampus; Brain, Occipital lobe; Brain, Parietal lobe; Brain, Temporal lobe; Breast; Cerebellum; Colon; Esophagus; Heart; Kidney; Liver; Lung; Muscle; Ovary; Pancreas; Placenta; Rectum; Skin; Small Intestine, duodenum; Small Intestine, Ileum; Small Intestine, Jejunum; Spleen; Stomach; Testis; Tonsil; Uterus, Cervix; and Uterus Corpus.

In order to precisely handle such high quantity of specimens of different origins in a high throughput manner, the secondary designated orders become critically important for identifying, tracing and correlating any detectable biological activities of the fractionated mRNA to its origin. Accordingly, based on the layout or the spatial arrangement of the fractions or fractionated molecules on the membrane of FIG. 1, any given fractions or fractionated molecules may be identified and traced based on the formula, $Fxy_i$, where F is the fraction of interest, x is the secondary designated order designating the origin of the fraction and $y_i$ is the primary designated order designating the initial migrating distance, order or timing of the fraction presented in the gel wherein i may be 1, 2, , , , to n, depending on the number of the fractions being cut from the gel. Thus, each fraction is assigned with a primary and a secondary designated order in the entire high throughput process that enables the handling of high quantity of specimens from different origins in an organized and precise manner.

Fractionated molecules in the gel fractions are recovered by means of gel extraction or elution. One group of serial fractionated molecules from one type of tissue, such as muscle, are arrayed on membrane supported by microscopic slide in the same order (the primary and secondary designated orders) as they are presented inside the gel and identified by their tissue types or origins as discussed above. In a preferred embodiment of the invention as further illustrated in FIG. 1, many groups of serial fractionated molecules from many different tissues, such as muscle, heart, brain, placenta, etc can be arrayed on the same membrane. Interactions of the fractionated mRNA or protein on membrane with gene specific probing molecules reveals the gene expression patterns among many tissues on the membrane. Molecular weight or size as the properties of mRNA and protein, to which the molecules are fractionated accordingly, can be measured and predicted, which are the crucial component of the gene expression patterns.

To provide mRNA ready to be fractionated is the first step to make HT Northern blot. The mRNA has to be isolated from total RNA. By way of illustration and not intended to be limited, total RNA from specimens such as human placenta tissue is isolated by conventional phenol extraction method. The isolation protocol is similar but not identical to the methods used by many other research laboratories and commercial methods. Total RNA is verified by gel electrophoresis and intact 28S and 18S rRNAs are obtained. The ratio of the 28S/18S is estimated to be around 2 from the intensity of the two bands. Further isolation and purification of mRNA is performed using oligo($dT_{12-18}$) cellulose columns. Because the two rRNA bands are dominant in total RNA preparation (85-90%), mRNA in the gel image is not visible. After purification and enrichment with the oligo(dT12-18), mRNA can be visualized in other locations of the gel while the intensities of the two rRNA bands are much decreased as seen in FIG. 2.

Many different methods can be employed to obtain fractionated mRNA populations, such as chromatography, HPLC or gel electrophoresis. Herein gel electrophoresis is employed for the purpose of illustrating this invention. mRNA isolated from human placenta is subjected to gel electrophoresis. 100 μg mRNA is diluted with DEPC-H2O to 100 μl. And a loading buffer containing MOPS, formamide and formaldehyde is added to the mRNA solution. The mixture is heated at 65° C. for 5 min and cooled down in ice. Ethidium bromide (100 μg/μl) is added before the sample is loaded on a 2.5 cm wide well of a 0.5 cm thick 1% formaldehyde agarose gel with a RNA molecular weight ladder (Life Technologies). The gel is run at 150 volt for about 3 hours till the front of bromophenol blue dye reaches exactly 10 cm. FIG. 2 shows the migration of mRNA in 1% formaldehyde agarose gel. The two rRNA bands can still be identified though the mRNA populations have been enriched by oligo(dT) selection. After washing the gel with 2×SSC, the gel is cut into 20 equally slices with each slice 0.5 cm exactly under UV illumination. The volume of each gel slice is 2.5 (wide)×0.5 (thickness)×0.5 (length)=0.625 $cm^3$. The slices are weighed to verify the size and collected into microcentrifuge tubes for mRNA extraction from the gel by a method described later. The distance and serial order of the fractionated gel slices was recorded and served as a primary designated order for applying fractionated RNA on microarray and data analysis.

Determination of molecular size of mRNA fractions has done by a combination of conventional method and mathematical calculation. Conventional method compares RNA ladder with known size and mRNA to be determined side by side relatively, and estimates molecular size of mRNA to be determined visually without referring exactly migration distance of mRNA. In this invention, we correlate the exactly migration distance and the size of RNA ladder to generate a mathematical formula, which will calculate exactly the molecular size of mRNA to be determined. Some technical issues will affect the accuracy of above calculation. For instance, the migration of the mRNA is dependent on the size or the mass of the molecules. mRNA is single nucleotide chain which is different from double stranded DNA, but mRNA molecules has a tendency to form complicated structures through intramolecular base pairing by its different regions, which will affect the migration distance of mRNA. Adding formamide to the loading buffer disrupts the formation of such structures. Thus the distance of the mRNA traveled from the initial point of the loading well can be only based on the size of mRNA. Therefore, the distance of the mRNA traveled can be mathematically fitted to the size of its mass or the number of nucleotides, and determines the size of mRNA that traveled.

By measuring the distances of each RNA size marker in RNA ladder, the known size of RNA marker (e.g. molecular weight or the number of nucleotides) and the distance (cm) from the well can be recorded (Table 1). Curve fitting the two parameters, we come up the following logarithm function:

$$Y=-2.1002\ Ln(x)+7.0839 \text{ with a } R^2=0.9917$$

Where X=number of nucleotides×1000, Y=cm of migration.

The fitted mathematical function has a $R^2=0.992$, indicating excellent fitting. The fitted curve is shown in FIG. 3. When different percentage of agarose gel is used and the running time is allowed to vary, the mathematical function can be similarly determined.

TABLE 1

Relation between size of RNA ladder and migration distance in gel

| Migration distance from loading well (Y), cm | Number of nucleotides (X), × 1000 Of each size marker in RNA ladder |
|---|---|
| 2.2 | 9.49 |
| 2.7 | 7.46 |
| 3.95 | 4.4 |
| 5.5 | 2.37 |
| 6.85 | 1.35 |
| 9.8 | 0.24 |

Based on the curve fitting function, we can further determine the molecular size of a RNA population migrated a certain distance from the loading well. The advantage of using such a function is one can always know the exact size of the genes once Y is determined on a particular gel. On the other hand, once the size of the gene of interest is known, one can expect the exact location of gene when hybridization is performed. Therefore, these calculations are the theoretical foundation to determine the RNA size in each fraction mentioned early or each spot on HT Northern blot described later.

Once the size of fractionated mRNA was determined and the primary and the secondary designated orders of fractionated were recorded, the fractionated mRNA can be recovered by extracting or eluting the fractionated mRNA from gel slices using a variety of methods, such as commercially available kits or devices. A commercial available kit, RNAID, from Qbiogene (Carlsbad, Calif.) is used to extract mRNA from the gel. Manufacturer recommended protocol is followed exactly. Briefly, mRNA containing gel slices are dissolved in a binding solution. After several times of washes, a RNA binding matrix is added and allow mRNA in the solution binds to the matrix. The matrix is washed again and finally it is eluted at 80.degree. C. in DEPC-H$_2$O and collected by centrifugation. Such recovery of mRNA from the gel can be performed using kits from other vendors such as Zymogen and Qiagen. An automated electroelution device from Bio-Rad may also be used.

Quantification of recovered mRNA is performed by UV spectrophotometry method. A portion of the recovered mRNA is added to a quartz cuvette and absorptions at 260 nm and 280 nm are measured. The amount of mRNA is directly related to the amount of UV light absorption at 260 nm when other conditions are the same. Depending on the size distribution of one certain mRNA preparation, some fractions may contain substantial more mRNA than the others. For example, fraction 12 may contain many times more mRNA than that of fraction 1. FIG. 4 shows the amount of each fraction recovered from 100 μg mRNA from 1% formaldehyde agarose gel. The total amount of mRNA recovered from the 20 fractions is 43.3 μg. Fractions 8 to 20 contain relatively more mRNA than that of fraction 1 to 7. This is consistent with the relative abundance of mRNA in different locations showed by FIG. 2.

To further confirm the property of fractionated mRNA after recovery from gel slices, same proportion of mRNA from each recovered fractions is applied onto an agarose gel to confirm the size or amount of recovered mRNA. When the fractionated mRNA are applied to 1% formaldehyde agarose gel and stained with ethidium bromide, each lane shows only one fraction of the original mRNA and the range of sizes of the mRNA fraction are as expected as shown in FIG. 5. The gel picture of fractionated RNA also shows the relative amounts and the intactness of fractionated mRNA fractions from human placenta mRNA. Fractions 8 to 20 contain more mRNA than the rest of the fractions. This is consistent with the relative abundance of mRNA in different locations showed by FIG. 2.

The fractionating, recovering and confirming processes as described above are exactly repeated on different specimens to generate different groups of fractionated molecules for further applications, comparison or analysis. As shown in FIG. 1, these processes are exactly repeated 31 times on mRNA from 31 different human tissues to generate different groups of fractionated mRNA molecules for HT Northern blot and further analysis. The 31 human tissues are listed as follows: Placenta; Bladder; Brain; Brain, Frontal lobe; Brain, Hippocampus; Brain, Occipital lobe; Brain, Parietal lobe; Brain, Temporal lobe; Breast; Cerebellum; Colon; Esophagus; Heart; Kidney; Liver; Lung; Muscle; Ovary; Pancreas; Placenta; Rectum; Skin; Small Intestine, duodenum; Small Intestine, Ileum; Small Intestine, Jejunum; Spleen; Stomach; Testis; Tonsil; Uterus, Cervix; and Uterus, Corpus.

As discussed above, a key element of the present invention is to arrange, format and present the recovered molecules from the serial fractions of gel slices into a serial spots on supporting material by and according to the primary and secondary designated orders recorded when the serial fractions of gel slices were made. It should be noted that much more mRNA samples could be applied on membrane to make a high throughput Northern blot if a higher density array instrument is used. However, for the purposes of illustration, only a limited mRNA samples are used to prove the concept. The recovered mRNA fractions from human placenta, bladder, brain and etc. are used as an example. A piece of supporting materials, such as positively-charged nylon membrane, is cut to exactly 1×2 inches and permanently fixed to a blank glass slide by two strips of double-sided tape at both ends of the membrane. A device from VP Scientific is used to make this low-density array. Each pin will pick up about 5 to 10 nl of solution and apply onto supporting membrane. As shown in FIG. 1, fractionated mRNA of all 20 fractions from human placenta mRNA sample is arrayed on one column consecutively according to the primary and secondary designated orders recorded when making fractionated gel slices. Fractionated mRNA of all 20 fractions from human liver mRNA sample is arrayed on other column consecutively according to the primary and secondary designated orders mentioned above also. Fractionated mRNA from other 29 different human tissues can be applied on this membrane by repeating the processes as did for fractionated mRNA from human placenta and liver mRNA. The order of tissues on blot from left to right are 1. Placenta; 2. negative control; 3. Bladder; 4. Brain; 5. Brain, Frontal lobe; 6. Brain, Hippocampus; 7. Brain, Occipital lobe; 8. Brain, Parietal lobe; 9. Brain, Temporal lobe; 10. Breast; 11. Cerebellum; 12. Colon; 13. Esophagus; 14. Heart; 15. Kidney; 16. Liver; 17. Lung; 18. Muscle; 19. Ovary; 20. Pancreas; 21. Placenta; 22. Rectum; 23. Skin; 24. Small Intestine, duodenum; 25. Small Intestine, Ileum; 26. Small Intestine, Jejunum; 27. Spleen; 28. Stomach; 29. Testis; 30. Tonsil; 31. Uterus, Cervix; and 32. Uterus, Corpus. The order of fractionated mRNA on the membrane from 31 different human tissues and one negative control is assigned and recorded with the primary and secondary designated orders. To permanently immobilize the mRNA onto the membrane, the membrane is UV cross-linked after the samples are applied onto it. Up to this stage, making of high throughput Northern blot is completed.

A probe for glyceraldehydes-3-phosphate dehydrogenase (GAPDH) is prepared by asymmetric PCR. A 410 bp portion of the human GAPDH gene is first amplified by RT-PCR using human spleen total RNA as the template. The PCR product is precipitated with 1/10 volume of 3 M sodium acetate and 3 volumes of ethanol. Then it is labeled by asymmetrical PCR with fluorescein-12-dUTP as the label. The PCR conditions for probe labeling are (final concentrations): 1×PCR buffer, 1.5 mM MgSO$_4$, 200 μM dATP, 200 μM dGTP, 200 μM dCTP, 100 μM dTTP, 100 μM fluorescein 12-dUTP, 0.04 unit/μl DNA polymerase, 0.5 μM reverse primer ng/μl template.

The membrane containing mRNA fractions is incubated in 20 ml of hybridization buffer for 30 min at 65° C. Fluorescein-labeled β-actin probe or GAPDH probe are denatured at 100° C. for 5 min and cooled down immediately in ice for another 5 min before it is added to the hybridization buffer at 1 μl/ml. The hybridization is carried at 65° C. overnight.

After hybridization, the membrane containing fractionated mRNA is first washed with a buffer containing 1×SSC and 0.1% SDS for 15 min at 65° C. followed by a wash with a buffer containing 0.1×SSC and 0.1% SDS for 15 min at 65° C. It is then blocked in 10% liquid block (Amersham Biotech) and 0.5% BSA in a buffer (buffer A) containing 0.3 M NaCl, and 0.1 M Tris-HCl, pH 9.5 for 30 min at room temperature. After blocking, the membrane is incubated at room temperature for 30 min in buffer A containing anti-fluorescein antibody (alkaline phosphatase conjugated) at 1:5000 dilution. The membrane is further washed three times in buffer A containing 0.3% Tween-20. Each wash is 10 min at room temperature. CDP-star solution is used for chemiluminescent detection of hybridization signals.

After the membrane containing fractionated mRNA from 31 different human tissues (HT Northern Blot) was hybridized with GAPDH probe, a variety of signals with different intensity were detected around fraction 13 among 31 tissues as shown in FIG. 6. According to the primary designated orders of fractionated gel slices and its migration distance mentioned above, mRNA size in fraction 13 is about 1.5× 1000 nucleotides that is corresponding to the mRNA size of GAPDH. The properties, which being the sizes of mRNA according to which the molecules are fractionated, are measured and predicted. Therefore, HT Northern blot according to the present invention has successfully analyzed gene size and gene expression patterns from a variety of tissues at the same time and under the same experimental conditions employing the membrane prepared for the high throughput Northern blot. The image data of HT Northern blot analysis can be collected directly from microarray scanner and converted into database. The computerized image of micro-array spots of each tissue can be enlarged for visualization by naked eyes as conventional Northern Blot also as shown in panel B, FIG. 6.

Example 1

The preparation and analysis of HT Northern blotting according to the present invention involves following steps, 1) isolation and purification of mRNA; 2) agarose gel electrophoresis of mRNA with RNA size ladder; 3) calculation of mRNA size based on migration distance of RNA size ladder; 4) fractionating of agarose gel with the mRNA into fractionated gel slices; 5) recording the distance and order of each of the fractionated gel slices as primary designated orders and recording the order of different specimens from which mRNA is isolated as secondary designated order; 6) recovering of fractionated mRNA from fractionated gel slices by extraction; 7) spotting fractionated mRNA onto support material according to each of the primary designated orders of fractionated gel slices and according to secondary designated order of different specimens, and 8) analysis of HT Northern blotting data according to the primary designated orders of fractionated gel slices and secondary designated order of different specimens.

Several examples and associated data are provided hereunder to further illustrate the above-listed steps. mRNA from 31 different human tissues were isolated and applied to agarose gel electrophoresis with RNA size ladder. FIG. 2 shows one of mRNA sample in agarose with RNA size ladder. A ruler measures the migration distance of RNA size ladder as well as mRNA sample. mRNA size is calculated based on the migration distance of mRNA mathematically as shown in FIG. 3. The agarose gel with mRNA was fractionated into 20 slices. The order from first slice to last slice with distance was each recorded as primary designated orders of fractionated gel slices. The fractionated mRNA was recovered from each gel slice as fractionated mRNA sample by extraction. Average recovery rate of fractionated mRNA is about 43% of mRNA from inside gel slices. Each fractionated mRNA sample fits the profiles of right size and right amount as shown in FIG. 4 and FIG. 5. Preparation of fractionated mRNA sample is completed and is ready for arraying.

Every fractionated mRNA samples from each tissue, containing 20 samples as illustrated by the embodiment according to FIG. 1, are applied onto membrane consecutively to form a column with 20 spots of fractionated mRNA samples. Repeat these steps for 32 times for the fractionated mRNA from 31 different tissues and one negative control. The order of fractionated mRNA on the membrane from 31 different human tissues and one negative control is assigned and recorded as the secondary designated order. After immobilization of spotted and fractionated mRNA samples on membrane, making of HT Northern Blot is completed.

A GAPDH probe was applied on this HT Northern Blot and a variety of signals with different intensity were detected around fraction 13 among 31 tissues according to secondary designated order as shown in FIG. 6. According to the primary designated orders of fractionated gel slices and its migration distance mentioned above, mRNA size in fraction 13 is about 1.5×1000 nucleotides that is corresponding to the mRNA size of GAPDH. The properties, which being the sizes of mRNA according to which the molecules are fractionated, are measured and predicted. Therefore, HT Northern blot according to the present invention has successfully analyzed gene size and gene expression patterns from a variety of tissues at the same time and under the same experimental conditions employing the membrane prepared for the high throughput Northern blot according to the primary designated orders and secondary designated order. The image data of HT Northern blot analysis can be collected directly from microarray scanner and converted into database. The computerized image of micro-array spots of each tissue can be enlarged for visualization by naked eyes as conventional Northern Blot as shown in panel B, FIG. 6.

Example 2

HT Northern blot analysis reserves the features of conventional Northern blot analysis, to determine the size of gene and the patterns of gene expression. FIG. 7 shows the results of comparison between both HT Northern blot analysis and conventional Northern blot analysis of GAPDH gene expression in mRNA from human placenta and human liver tissues. Panel A shows the result from HT Northern blot analysis. Four spots on the left side of panel A with relatively strong signals are GAPDH in human placenta mRNA and the weak signals on the right side are GAPDH expression in human liver. The expression patterns of HT Northern blot analysis are in consistency with our observation with conventional Northern blot analysis (Panel B). The spots with the strong signals in HT Northern blot (panel A) are around fraction 13 of the 20 fractions of mRNA. Fraction 13 contains mRNA populations migrated 6.0 to 6.5 cm from the loading well in the 1% agarose gel with formaldehyde, which approximately corresponding to 1.5×1000 nucleotides in length of mRNA. This is indeed the range the estimated GAPDH mRNA size should be. Thus, this experiment confirms our method conserves the two prominent features of Northern blot, such as estimating the sizes of the target genes and measuring the levels of the gene expression in a particular sample.

Example 3

Higher sensitivity in detection of gene expression is the one of the great advantages of HTS Northern blot analysis over conventional Northern blot analysis, which is confirmed in this invention. One limitation of application for Northern blot is the sensitivity of the method. Usually a few micrograms of mRNA is loaded to a lane about 5 mm wide and 5 mm thick. Average amount of mRNA applied on conventional Northern Blot is about 2 µg. Rarely more than 10 µg of mRNA is loaded for commercially Northern blot membranes since the amount is approaching the limit of the gel capacity and otherwise the separation of RNA is not acceptable. The capacity of each lane on the agarose gel with formaldehyde is limited for mRNA. The capacity is dependent on the gel thickness, the width of the gel and the formulation of the gel. Besides the amount of mRNA can be loaded on to each lane of the gel, sensitivity of Northern blot analysis also depends on the binding capacity of the transfer membrane, the transfer efficiency, and the detection process.

In order to compare the sensitivities of detection between conventional Northern blot and HT Northern blot techniques, two identical gels with mRNA were made by electrophoresis to create a comparable condition. On each gel, 0.3 µg and 3 µg mRNA from rat lung is loaded on 1% agarose gel with formaldehyde in two lanes to perform electrophoresis. One gel is for conventional Northern blot and the other gel for HT Northern blot. To make conventional Northern blot, mRNA in one gel is transferred to positively charged nylon membrane (Hybond N+ from Amersham Biotech) by vacuum transfer apparatus as routine. For HT Northern blot, the other gel with mRNA was fractionated into 20 slices after electrophoresis. Fractionated mRNA was recovered from 20 gel slices. Total amount of recovered mRNA from each gel slice was spotted onto positively charged nylon membrane (Hybond N+ from Amersham Biotech) to mimic the conditions of conventional Northern blot in term of equivalent amount of starting mRNA applied on gel electrophoresis. Both membranes are subjected to UV cross-linking and subsequent hybridization and detection with GAPDH probe under exactly same conditions.

HT Northern blot analysis shows much higher sensitivity in detection of gene expression, such as GAPDH, than the conventional Northern blot analysis. As shown In Panel B of FIG. 8 the signal from 0.3 µg of starting mRNA on conventional Northern blot analysis is barely visible compared to significant signal generated by 0.3 µg of starting mRNA from HT Northern blot analysis in Panel A. The 3 ug starting mRNA in conventional Northern blot is showing the same result as 0.3 ug of starting mRNA does in HT Northern blot. Some factors may contribute to this high sensitivity of HT Northern blot analysis, such as higher recovery efficiency of mRNA from gel by extraction (43% as mentioned before) than by vacuum transfer as in conventional Northern blot, smaller area bound by spotting fractionated mRNA that generates higher density of spot than vacuum transferred mRNA as in conventional Northern blot, or higher affinity of mRNA bound to membrane by directly spotting in dry condition than vacuum transferred under wet and salty condition as in conventional Northern blot.

Beside the capability to detect expression of gene with lower copy that is undetectable by conventional Northern blot, the other great advantages of this invention is to use less molecules or materials to perform high throughput Northern blot analysis due to the advantage of high sensitivity of detection. This is extremely important because molecules, such as mRNA, have very limited resource and are very hard to obtain. Therefore, this invention created the possibilities to detect molecules that are undetectable by conventional method, as well as to perform detection on molecules that have limited resource by saving the molecules.

Example 4

As example, one of other applications of this invention is High Throughput Western blot analysis. The principle to perform High Throughput Western blot analysis is the same as High Throughput Northern blot analysis while the method to fractionate protein is different. Total tissue proteins are extracted from frozen human tissues using a homogenization buffer containing detergents and a cocktail of protease inhibitors. To fractionate the protein, 1.25 mg of total tissue proteins is loaded onto a 4-20% Tris-glycine SDS-PAGE gel (Criterion gel, from Bio-Rad Laboratories). The proteins can be recovered by different methods, such as extraction from gel slices as did in HT Northern blot, or electronic elution out of gel by instrument. In one embodiment, of the present invention the Whole Gel Eluter (Bio-Rad Laboratories) is used to elute fractionated protein out of gel. The elution buffer contains 25 mM Tris-HCl, 192 mM glycine, and 0.1% SDS. The eluted fractions are collected by vacuum aspiration. The size of Criterion gel is 13.3×8.7 (W×L) cm. When 0.5 cm gel length is used for each fraction collection, 16 fractions that contain fractionated proteins per tissue sample can be recovered. The primary designated orders and secondary designated order are recorded in this step for 16 different human tissues. Proteins in these fractions are concentrated using Amicon (Millipore) tubes to the same volume. To verify good separations between each fraction, recovered fractions are loaded onto the same type of gel and run at the same conditions. FIG. 9 shows recovered fractionated proteins stained with Coomassie brilliant blue in gel.

The same microarray device is used to apply the fractionated proteins to membranes consecutively according to the primary designated orders. The order of 16 different human tissues representing each group of fractionated protein recovered and arrayed on membrane is according to assigned and recorded primary and secondary designated order. Glyceraldehyde-3-phosphate dehydrogenase is used as a target protein for HT Western blot analysis. After blocking the membrane with 5% fat-free milk in TBST (0.1% Tween 20 in TBS), mouse anti-GAPDH monoclonal antibody (MAB374, Chemicon International) is added to TBST and is used to incubate with the membrane overnight at 4° C. After three rounds of washing with TBST, HRP conjugated anti-mouse-IgG (NA 931, Amersham Biotech) is added and the signal is detected by using ECL-plus (Amersham Biotech). FIG. 10 shows an example of 32 lanes HT Western blot using protein fractions recovered from 16 different tissue proteins in duplicates. The tissues are: from left to right 1,2 heart, 3,4 brain, 5,6 kidney, 7,8 liver, 9,10 lung, 11,12 pancreas, 13,14 spleen, 15,16 skeletal muscle, 17,18 stomach, 19,20 small intestine, 21,22 colon, 23,24 rectum, 25,26 uterus, 27,28 prostate, 29,30 testis, and 31,32 placenta. At expected molecular weight of 38 kDa, GAPDH is detected in fraction 9 of a total of 16 fractions according to the primary designated orders. The properties, which being the sizes of protein according to which the molecules are fractionated, are measured and predicted. A variety of signals with different intensity indicate that 16 different human tissues express different amount of GAPDH protein according to secondary designated order as shown in FIG. 10.

Example 5

Since the present invention adopts the microarray format, it is rather easy to see that it has high throughput performance capabilities. FIG. 6 and FIG. 10 show respectively two examples of high throughput Northern blot and high throughput Western blot, each showing 32 samples arrayed on a 1×2 inch membrane comparing with conventional methods in which around 10 samples can be analyzed on a 2×4 inch membrane. However, it should be emphasized that the number of samples applicable pursuant to the present invention are by no mean limited to the examples. For instances, a high-density microarray can have over 500,000 spots per membrane. Thus, depending on the number of fractions to be applied per sample, microarray with high density should provide even more powerful high throughput capability to this invention. If each sample is fractionated to 50 fractions, 10,000 samples can be arrayed to one single membrane. Accordingly, the present invention provides a high throughput Northern blot analysis or Western blot analysis with a capacity of handling, for example, 10,000 tissue samples on a single membrane. In addition, the large amount of data generated from above high throughput analysis can be collected directly by microarray scanner and converted into database, which is almost impossible for conventional Northern blot analysis or Western blot analysis.

It can be concluded from above descriptions and examples that this invention presents the high throughput (HT) analysis technology for molecular fractions that uses micro-array or macro-array format, which combined the unique features of molecular fractionating technique and the power of micro-array or macro-array to achieve certain criticality and new advantages that are not expected from the conventional molecular fractionating technique. Beyond the feature of conventional molecular fractionating technique this invention creates a more sensitive method while consuming less treasured materials. The most important of the benefit is that up to hundred or thousands of samples can be analyzed in a high throughput way for molecular fractions, such as alternative splicing or sizing of a specific gene among hundreds of different tissues, on a micro-array or macro-array. Furthermore, the information about molecular fractions can be digitized and collected directly by array scanner and convert into database, and data analysis can be accommodated into micro-array detection technology platform. Currently there are no methods that can meet such extreme technological demanding. The invention therefore represents a major innovatory change in analysis of molecular fractions, especially for Northern/Western blot analyses.

The invention has been described using exemplary preferred embodiments. However, for those skilled in this field, the preferred embodiments can be easily adapted and modified to suit additional applications without departing from the spirit and scope of this invention. Thus, it is to be understood that the scope of the invention is not limited to the disclosed embodiments. On the contrary, it is intended to cover various modifications and similar arrangements based upon the same operating principle. The scope of the claims, therefore, should be accorded the broadest interpretations so as to encompass all such modifications and similar arrangements.

We claim:

1. A method of analyzing a plurality of molecular fractions from a population of molecules from or within the same or different origin(s) in high throughput manner, comprising the steps of:
   (1) fractionating each of said plurality of molecular fractions into a spectrum or a group of serial fractions containing sub-populations of serial fractionated molecules according to properties of said serial fractionated molecules in fractionating media wherein each of said spectrum or said group of serial fractions is assigned a primary designated order relating to said fractionating and a secondary designated order relating and corresponding to the same or different origin(s);
   (2) recovering the serial fractionated molecules from the fractionating media wherein each of the recovered serial fractionated molecules is accorded with the same primary and secondary designated orders assigned in step (1) to each of said group of serial fractions from which it is recovered;
   (3) arraying said recovered serial fractionated molecules onto a solid substrate according to their corresponding primary and secondary designated orders in step (2);
   (4) designing and selecting probing molecules that can interact and bind to the recovered serial fractionated molecules arrayed on the supporting material in step (3), followed by performing incubation or hybridization of the probing molecules with the recovered serial fractionated molecules arrayed on the supporting material in step (3) to generate presentation patterns;
   (5) analyzing and correlating the presentation patterns according to the corresponding primary and secondary designated orders of the arrayed recovered serial fractionated molecules, wherein said analyzing and correlating is performed by mathematic calculation, and computerized image and data analysis in a high throughput way to generate a database, wherein said correlating correlates each of the arrayed recovered serial fractionated molecules to said fractionating and said same or different origin(s); and
   (6) measuring the properties of said serial fractionated molecules; and
   wherein said method of analyzing is used for detection of nucleic acid, protein, or peptide, and said molecules are nucleic acids, proteins, or peptides.

2. The method of claim 1 wherein step (4) further comprises a step of detecting the amount of the incubated or hybridized probing molecules bound to the molecules on the substrate after said incubation or hybridization by a detection means.

3. The method of claim 2, wherein the step of detecting the amount of the incubated or hybridized probing molecules is performed manually or by instrument.

4. The method of claim 1, wherein the molecular fractions are mixtures of similar or different molecules with similar or different properties capable of being fractionated into a spectrum or a group of serial fractions after a fractionating process.

5. The method of claim 4, wherein the fractionated molecules include nucleic acid, protein, peptide, lipid, or polysaccharides.

6. The method of claim 1, wherein the properties of said serial fractionated molecules in step (1) is selected from the group consisting of molecular size, charges, solubility, weight, density, affinity to the fractioning media, mass and color.

7. The method of claim 1, wherein the fractionating in step (1) is performed by fractionating means selected from the group consisting of agarose gel electrophoresis, polyacrylamide gel electrophoresis (PAGE), two-dimension PAGE, isoelectrical focusing, ion exchange chromatography, filtration chromatography, hydrophobic chromatography, high performance liquid chromatography (HPLC), thin layer chromatography (TLC), gas chromatography, atomic absorption, affinity chromatography and gradient centrifugation.

8. The method of claim 7, wherein the fractionating in step (1) is performed by a combination of two or more fractionating means defined in claim 7.

9. The method of claim 1, wherein the primary designated order is assigned according to the migration distances of the fractioned molecules in said fractionating media or the timing of the fractioned molecules run-out from said fractionating media.

10. The method of claim 1, wherein the fractionating in step (1) is performed based on an arbitrary set of cut-off points of the fractionated molecules referred by companying molecular weight standards.

11. The method of claim 10 wherein the arbitrary set of cut-off points can be set in a linear, logarithm, or exponential relationship of said companying molecular weight standards to the fractionated molecules.

12. The method of claim 1, wherein the primary designated order in step (1) is a natural order formed by said group of serial fractions or is a rearranged order.

13. The method of claim 1, wherein the recovering in step (2) is optionally performed by not separating the serial fractionated molecules from said fractionating media.

14. The method of claim 1, wherein the recovering in step (2) is automated.

15. The method of claim 1, wherein the recovering in step (2) is assisted by a commercially available kit or device.

16. The method of claim 1, wherein the arraying in step (3) is performed by using a micro-arrayer or manually with or without a device.

17. The method of claim 1, wherein the total number of the fractions containing fractionated molecules with the primary designated orders is from two to 500,000 fractions for about 2 square inch of the supporting material.

18. The method of claim 1 wherein arraying said recovered serial fractionated molecules in step (3) is optionally performed in an arbitrary order.

19. The method of claim 1, wherein the supporting material in step (3) is selected from the group consisting of nitrocellulose, nylon, plastic, glass, multi-well plates and beads.

20. The method of claim 19 wherein the supporting material is further treated to have a charge, is chemically modified to carry molecule binding enhancer, or is silylated or silanated.

21. The method of claim 1, wherein the probing molecules in step (4) is RNAs, DNAs, proteins, antibodies or chemically modified proteins with a chemical label, fluorescent label or radioactive isotope.

22. The method of claim 1, wherein the incubation or hybridization of the probing molecules is performed either manually or automatically.

23. The method of claim 1, wherein the mathematic calculation determines the migration distance or run-out time of the serial fractionated molecules in or from the fractionating media according to the primary designated orders in step (1) of claim 1.

24. The method of claim 1, wherein the computerized image and data analysis determines the amount of each of the serial fractionated molecules according to the primary designated orders and the secondary designated orders in step (1) of claim 1.

25. The method of claim 1, wherein the computerized image and data analysis enlarges an image of arrayed spots of each of the serial fractionated molecules.

26. The method of claim 1, wherein the arraying in step (3) generates stronger signals to increase detection sensitivity compared to conventional Northern blot analysis or Western blot analysis.

27. The method of claim 1 wherein the computerized image and data analysis can directly collect, analyze and convert information from the fractionated molecules into a database, which can not be achieved by the conventional Northern blot analysis or Western blot analysis.

28. A method of generating molecular fractions from a population of molecules from or within the same or different source origin(s) suitable for further manipulation in a high throughput manner, comprising the steps of:
  (1) providing a plurality of molecular fractions from said origin(s) in a form ready to be fractionated;
  (2) fractionating each of said plurality of molecular fractions into a spectrum or a group of serial fractions containing sub-populations of serial fractionated molecules according to properties of said serial fractionated molecules in fractionating media wherein each of said spectrum or said group of serial fractions is assigned a primary designated order and a secondary designated order;
  (3) recovering the serial fractionated molecules from the fractionating media wherein each of said serial fractionated molecules is accorded with the same primary and secondary designated orders in step (2) as each of said group of serial fractions from which it is recovered;
  (4) arraying said recovered serial fractionated molecules onto a supporting material according to their corresponding primary and secondary designated orders in step (2) to be manipulated further in a high throughput manner; and
  wherein said molecules are nucleic acids, proteins, or peptides.

29. A method of profiling representation patterns of molecular fractions prepared from a variety of different source origins in a high throughput manner, comprising the steps of:
  (1) providing a plurality of molecular fractions from said variety of different source origins in forms ready to be fractionated;
  (2) fractionating each of said plurality of molecular fractions into a spectrum or a group of serial fractions containing sub-populations of serial fractionated molecules according to properties of said serial fractionated molecules in fractionating media wherein each of said spectrum or said group of serial fractions is assigned a primary designated order and a secondary designated order;
  (3) recovering the serial fractionated molecules from the fractionating media wherein each of said serial fractionated molecules is accorded with the same primary and secondary designated orders in step (2) as each of said group of serial fractions from which it is recovered;
  (4) repeating step (2) and step (3) for each of said variety of different source origins until fractionation and recovery of all fractions of said variety of different source origins are completed;
  (5) arraying said recovered serial fractionated molecules from said variety of different source origins onto a supporting material according to their corresponding primary and secondary designated orders in step (2) to continue in step (6) or to be manipulated further later;
  (6) designing and selecting probing molecules intended to interact with the serial fractionated molecules arrayed on the supporting material in step (5) to obtain representation patterns of the arrayed fractionated molecules from said variety of different source origins;
  (7) analyzing and comparing said representation patterns of the arrayed fractionated molecules from said variety of different source origins according to their corresponding primary and secondary designated orders in step (2);
  (8) measuring the properties of said fractionated molecules; and
  wherein said molecules are nucleic acids, proteins, or peptides.

30. The method of claim 29, wherein the variety of different source origins comprise human tissues selected from the group consisting of placenta, bladder, brain, frontal lobe of brain, hippocampus of brain, occipital lobe of brain, parietal lobe of brain, Temporal lobe of brain, breast, cerebellum, colon, esophagus, heart, kidney, liver, lung, muscle, ovary, pancreas, rectum, skin, small intestine, duodenum, Ileum of the small intestine, Jejunum of the small intestine, spleen, stomach, testis, tonsil, uterus, cervix; and uterus corpus.

* * * * *